(12) United States Patent
Delamarche et al.

(10) Patent No.: US 10,155,923 B2
(45) Date of Patent: Dec. 18, 2018

(54) MICROORGANISM CULTURE DEVICE AND METHOD OF OPERATION THEREOF

(75) Inventors: Emmanuel Delamarche, Thalwil (CH); Robert Lovchik, Schoenenberg (CH)

(73) Assignee: International Business Machines Corporation, Armonk, NY (US)

( * ) Notice: Subject to any disclaimer, the term of this patent is extended or adjusted under 35 U.S.C. 154(b) by 297 days.

(21) Appl. No.: 13/257,320

(22) PCT Filed: Mar. 4, 2010

(86) PCT No.: PCT/IB2010/050941
§ 371 (c)(1),
(2), (4) Date: Oct. 26, 2011

(87) PCT Pub. No.: WO2010/106456
PCT Pub. Date: Sep. 23, 2010

(65) Prior Publication Data
US 2012/0034677 A1 Feb. 9, 2012

(30) Foreign Application Priority Data
Mar. 20, 2009 (EP) ..................................... 09155694

(51) Int. Cl.
*C12M 3/06* (2006.01)
*B01L 3/00* (2006.01)

(52) U.S. Cl.
CPC ....... *C12M 23/16* (2013.01); *B01L 3/502723* (2013.01); *B01L 2200/0642* (2013.01);
(Continued)

(58) Field of Classification Search
CPC .............................. C12M 23/12; C12M 23/16
See application file for complete search history.

(56) References Cited

U.S. PATENT DOCUMENTS 4,722,598 A 2/1988 Ford
6,818,435 B2 * 11/2004 Carvalho et al. .......... 435/286.5
(Continued)

FOREIGN PATENT DOCUMENTS

| EP | 0133286 A1 | 2/1985 |
| EP | 1333286 A1 | 8/2003 |

(Continued)

OTHER PUBLICATIONS

Sung Jae Kim, et al., "Self-Sealed Vertical Polymeric Nanoporous-Junctions for High-Throughput Nanofluidic Applications", Analytical Chemistry, 2008, 80 (9), 3507-3511.
(Continued)

*Primary Examiner* — Jonathan M Hurst
(74) *Attorney, Agent, or Firm* — Heather S. Chatterton (57) ABSTRACT

A microorganism culture device and a method of using the device. The device includes an open chamber, wherein microorganisms are likely to be deposited within a liquid for subsequent study. The open chamber simplifies the deposition of the microorganisms. The chamber is further provided with retention features, whereby microorganisms can be retained therein. In addition, the device includes an overflow area, wherein capillary structures are configured to retain excess liquid overflowing from the open chamber, e.g. when covering the device with a cover. As such, it allows for confining microorganism in the chamber, while excess fluid is captured externally, e.g. to seal the device with a cover.

14 Claims, 5 Drawing Sheets

(52) U.S. Cl.
CPC .......... *B01L 2300/0816* (2013.01); *B01L 2400/0406* (2013.01); *B01L 2400/084* (2013.01)

(56) References Cited

U.S. PATENT DOCUMENTS

| | | | |
|---|---|---|---|
| 7,138,270 | B2 | 11/2006 | Papkovsky et al. |
| 7,351,575 | B2 | 4/2008 | Duffy et al. |
| 2004/0241783 | A1 | 12/2004 | Papkovsky et al. |
| 2004/0265172 | A1 | 12/2004 | Pugia et al. |
| 2007/0026469 | A1* | 2/2007 | Fuchs .............. B01L 3/502707 435/7.23 |
| 2007/0090166 | A1 | 4/2007 | Takayama et al. |
| 2007/0264705 | A1* | 11/2007 | Dodgson .................... 435/283.1 |
| 2011/0117634 | A1* | 5/2011 | Halamish ............... C12M 23/12 435/283.1 |

FOREIGN PATENT DOCUMENTS

| | | |
|---|---|---|
| JP | 2008519598 | 6/2008 |
| WO | WO 0225289 | 3/2002 |

OTHER PUBLICATIONS

Lovchik et al., "Overflow Microfluidic Networks for Open and Closed Cell Cultures on Chip", Analytical Chemistry, 2010, 82 (9), 3936-3942.

Lovchik et al., "Controlled deposition of cells in sealed microfluidics using flow velocity boundaries", Lab on a Chip, Published Feb. 23, 2009, Copyright The Royal Society of Chemistry 2009, 8 pages, DOI: 10.1039/B820198F. www.rsc.org/loc.

Zimmermann et al., "Capillary pumps for autonomous capillary systems", Lab on a Chip, Published Oct. 17, 2006, Copyright The Royal Society of Chemistry 2007, 7 pages, DOI: 10.1039/B609813D. www.rsc.org/loc.

* cited by examiner

MICROORGANISM CULTURE DEVICE AND METHOD OF OPERATION THEREOF

CROSS-REFERENCE TO RELATED APPLICATION

This is a U.S. National Phase application which claims priority from International Application PCT/IB2010/050941, filed Mar. 4, 2010, which in turn claims priority from European Patent Application No. 09155694.4, filed on Mar. 20, 2009. The entire contents of both of these applications are incorporated herein by reference.

FIELD OF THE INVENTION

The invention relates in general to the field of microorganism culture devices, and in particular, to microfluidic devices for cell culture.

BACKGROUND OF THE INVENTION

The culture of microorganisms is in use in biological sciences, clinical sciences, and biotechnology. It makes use of microorganism culture devices.

Living cells are an example of microorganisms broadly used in biology. First, the most common culture method involves culture on the bottom of a Petri dish or T flask. With such devices, the presence of liquid and an uneven air-liquid/cell interface may impair the imaging of the cells when using e.g. upright microscopes. Cells can otherwise be observed using an inverted microscope as the bottom of the culture dish provides a well defined optical interface. Yet, at high magnification (>40x), the depth of focus becomes a concern. A thin coverslip is often placed over (upright microscope) or possibly below (inverted microscope) the cells. Placing the coverslip requires experimental skills in order not to e.g. squeeze cells, entrap a thick layer of liquid, or create leaks between the coverslip and the culture dish. Furthermore, samples with a coverslip cannot be reused. Therefore cells are difficult to observe with the most common culture methods.

Second, it might be advantageous to culture and study cells in microfluidics, as known in the art, because (i) it lowers costs for rare cells or cells difficult to culture, (ii) it enables better cell proliferation studies, (iii) cells have a better (smaller) ratio cells/volume of surrounding medium, and (iv) a faster exchange of nutrients and stimulating factors can be achieved. Some of these advantages are for instance described in A. Persidis, *Nature Biotechnol.*, 1998, 16, 488-489.

In this respect, many microfluidic systems are made of polydimethylsiloxane (PDMS), due to its favorable mechanical properties, optical transparency, and bio-compatibility. Complex microfluidic cell culture devices have been for instance developed for diverse cell types such as Eukaryotic cells, lung cells, embryonic stem cells, and mammalian embryos. In particular, microfluidics are used for trapping and culturing cells: cells must be retained in specific areas that are suited for measurements; they may further need regular exchange of medium, controlled temperature and $CO_2$. In addition, some critical cells (e.g. neurons) are difficult to culture in such systems because they need several days for attaching and developing a phenotype.

For the sake of exemplification thereof, let mention that US 2007/0090166 discloses a micro fluidic device which includes a substrate and membrane. The substrate includes a reservoir in fluid communication with a passage. A bio-compatible fluid may be added to the reservoir and passage. The reservoir is configured to receive and retain at least a portion of a cell mass. The membrane acts as a barrier to evaporation of the bio-compatible fluid from the passage. A cover may be added to cover the bio-compatible fluid to prevent evaporation of the bio-compatible fluid.

Next, US 2004/0265172 is directed to a microfluidic device for analyzing biological samples. The device is provided with a sample inlet section including an inlet port, a capillary passageway communicating with the inlet port and with an inlet chamber. The inlet chamber includes means for uniformly distributing the sample liquid across the inlet chamber and purging the air initially contained therein.

Somehow related, U.S. Pat. No. 7,138,270 discloses an assay device that comprises a base and glass plate lid. The base has an array of shallow microwells, each having a flat rim, all rims being co-planar. When the lid is placed on the base, a thin capillary gap is formed on each rim, acting as a liquid seal for a microwell chamber. The liquid is excess sample liquid and further excess is accommodated in overspill cavities between the microwells. Because of the liquid seal and shallow configuration the benefits of micro fluidic devices are achieved together with the handling convenience and use of conventional detection equipment of conventional microplate devices. As the lid is placed on the base, excess sample overspills into the surrounding overspill areas. A residual amount of sample fills a capillary gap between the rim and the lid. Therefore, the desired volume of the sample is completely surrounded by the base and the lid without any ambient air contact. The excess sample is on the rim forming the microchamber seal, and in the overspill cavities. Contact of the lid and the frames forms a second level of enclosure, also limiting access by ambient air and minimizing sample evaporation and contamination. The vents ensure uniform placement of the lid by allowing ambient air to escape as the overspill cavities receive excess sample during placement of the lid.

Also, U.S. Pat. No. 7,351,575 discloses a method for performing at least one bulk process step on a biological material comprising: a) chemically treating a base plate to enhance immobilization of kinase substrates thereon with a solution of mixed self-assembled monolayer (SAM) comprising about 0.1 to 20% maleimide-terminal groups in a background of tri(ethylene glycol) terminal groups; b) placing a first removable member on the base plate for establishing self-sealing contact of the first removable member on the base plate, the first removable member being adapted to repeatedly self-seal on the base plate, the first removable member further defining a plurality of first orifices therein, each having a plurality of first walls bounding respective ones of the plurality of first orifices, the first removable member further being configured such that, when placed in self-sealing contact with the base plate, the first removable member defines a plurality of first wells therewith corresponding to respective ones of the plurality of first orifices. The removable member is formed of a material capable of spontaneously forming a fluid-tight seal with surface when placed into contact therewith. A fluid-tight seal is achieved without the use of adhesives, ultrasound, heat or other means. The removable member is capable of being sealed to the surface, then removed (by means such as peeling and lifting, which may be performed manually or by machine) without damaging or leaving residue on the surface.

Beside the sole patent literature, a number of publications are devoted to the subject, amongst which a paper of Sung Jae Kim, et al., "Self-Sealed Vertical Polymeric Nanoporous-Junctions for High-Throughput Nanofluidic Applications", ACS Publications. Here, the authors have developed an integration method of polymeric nanostructure in a poly(dimethylsiloxane) (PDMS)-based microfluidic channel, for nanofluidic applications. The polymer junction was created by infiltrating polymer solution between the gaps created by mechanical cutting, without any photolithography or etching processes. The PDMS can seal itself with the heterogeneous polymeric nanoporous material between the PDMS/PDMS gap due to its flexibility without any (covalent) bonding between PDMS and the polymer materials. Thus, it is possible to integrate the nanoporous junction into a PDMS microchip in a leak-free manner with repeatability.

BRIEF SUMMARY OF THE INVENTION

According to a first aspect, the present invention is embodied as a microorganism culture device, comprising: an open chamber having microorganism retention features; and an overflow area, comprising capillary structures configured to retain, in operation, excess liquid overflowing from the open chamber.

In other embodiments, the said device may comprise one or more of the following features:
- the overflow area is an open area, the chamber and the overflow area have a same open side; the device further comprises a cover, preferably transparent, movable to a close position where it covers the open side, and the capillary structures are further configured such that liquid retained therein retains the cover in the close position, by capillarity;
- the device is configured such that the cover is self sealable on the device;
- the chamber comprises one or more liquid passages allowing closed circulation of the liquid inside the device; and the cover comprises one or more vias connectable to the passages in the close position;
- the capillary structures define a lattice allowing for filling at least 30% or preferably 50% of a surface of the lattice with liquid retained in the lattice;
- an average separation distance of the capillary structures is less than 500 µm, preferably 200 µm, and more preferably 60 µm;
- the chamber further comprises one or more distribution structures configured to distribute a liquid flow in the chamber;
- the device is a microfluidic culture device;
- the device further comprises vents configured to remove, in operation, excess fluid from the capillary structures;
- the overflow area is substantially at a periphery of the chamber; and
- the device further comprises a dewetting zone between the chamber and the overflow area, wherein a capillary pressure is lower than a capillary pressure in the overflow area, in absolute term.

The invention is further directed, in another aspect, to a method for operating a microorganism culture device, comprising: providing a cover and a device according to the invention, and a liquid comprising microorganisms; filling the open chamber with the liquid in excess, such that a liquid portion protrudes from the open chamber; and covering the device by pressing the protruding portion of the liquid with a cover, such that liquid in excess overflows from the chamber to the overflow area, to be retained therein.

In further embodiments, the said method may comprise one or more of the following features:

- the step of covering further comprises moving the cover to a close position wherein liquid retained in the overflow area retains the cover by capillarity;
- the method further comprises the steps of: removing the cover; intervening in the device; and covering again the device with the cover;
- at the step of providing, the chamber of the device comprises one or more passages allowing closed circulation of a liquid in the device and the cover comprises one or more vias connectable to the passages in the close position; and at the step of closing, the vias are connected to the passages; and
- the method further comprises the steps of: introducing a sample in the chamber through at least one of the vias; and monitoring the liquid interacting with the sample.

A device and method embodying the present invention will now be described, by way of non-limiting example, and in reference to the accompanying drawings.

Be it for the sake of clarity, details shown in the figures (especially FIGS. 1-6) may purposely be exaggerated, simplified, or truncated, and are not necessarily to scale.

DETAILED DESCRIPTION OF THE INVENTION

As an introduction to the following description, it is first pointed at general aspects of the invention, directed to a microorganism culture device. The device comprises an open chamber, wherein microorganisms are likely to be deposited within a liquid for subsequent study. Having an open chamber simplifies the deposition of the microorganisms and furthermore allows for using standard instruments as used for e.g. cell culture. The chamber is yet provided with retention features, whereby the microorganisms can be retained therein.

Remarkably, the device further comprises an overflow area, wherein capillary structures are configured to retain excess liquid overflowing from the open chamber, e.g. when covering the device. Thus, the devices exhibits distinct areas, one is dedicated to the culture of microorganisms retained therein, while the other is designed to capture the excess liquid. As such, it allows for confining reagent in the chamber, the latter behaving as a filter. Excess fluid is captured externally for other applications. In particular, the captured liquid may be used for closing the device with a cover, by capillarity. Embodiments described hereafter make it notably possible to reduce the formation of air bubbles and/or prevent inefficient sealing due to excess liquid. This is advantageous notably for miniaturized assays.

For the sake of exemplification, the embodiments of the present invention that are described below shall mostly refer to cell culture. However, it shall be apparent to those skilled in the art that other microorganisms can be contemplated in the context of the invention. Examples are: bacteria, cells or bacteria infected with viruses, pluricellular organisms or more advanced organisms such as nematodes (e.g. *Caenorhabditis elegans*) and eggs.

Figure 1:
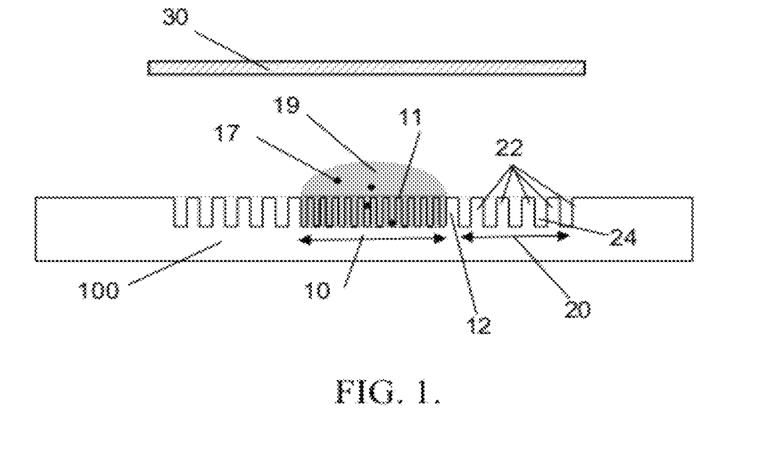
FIGS. 1-3 schematically depict cross-sectional views of a microorganism culture device, according to an embodiment of the present invention, and at different stages of operation thereof.
Figure 4:
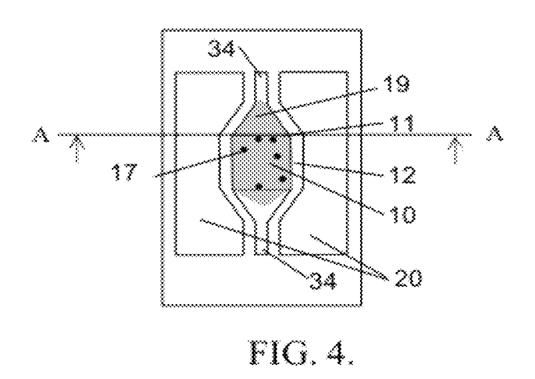
FIGS. 4-6 shows 'head-on' schematic views of the same device, corresponding to the sectional views of FIGS. 1-3, respectively.

FIG. 1 schematically depicts a sectional view of a device according to an embodiment, and corresponding to the elevation view of FIG. 4. The section in FIG. 1 actually corresponds to the line A-A shown in FIG. 4.

In reference to both FIGS. 1 and 4, a culture device 100 shows an open chamber 10, wherein retention features 11 are provided for retaining e.g. living cells 17 or any other microorganism deposited therein. Apart from the retention features 11, the chamber may typically comprise lateral walls 12 delimitating it.

The device further comprises an overflow area 20, having capillary structures 22 which defines capillary recesses 24. As shall be more clearly illustrated in reference to FIGS. 3-6, the capillary structures are notably configured to retain excess liquid 19 overflowing from the open chamber 10.

For the time being, no overflow is to be seen yet, as the liquid 19, e.g. a suspension of cells 17, has just been filled in the chamber. The suspension is likely deposited with a micropipette, which is easily carried out from the open side of the chamber.

As depicted in FIG. 1, the liquid 19 and chamber 10 are preferably chosen such that surface tension results in a convex meniscus extending above the chamber, i.e. a liquid portion protrudes from the open chamber.

A cover (or lid) 30 can further be provided (see FIG. 1, not shown in FIG. 4), as to be discussed now.

Figure 2:
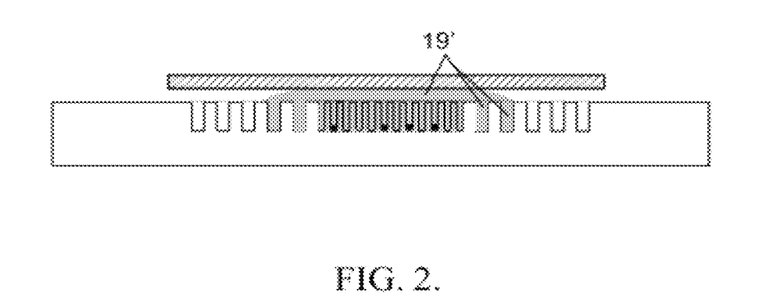
Figure 5:
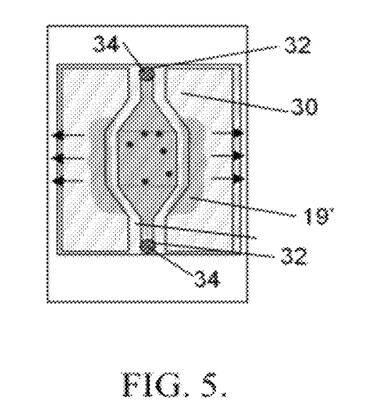

Turning to FIG. 2 or 5, the cover 30 can be moved towards the device. Basically, the cover is manipulated such as to press the protruding liquid portion, such that an excess of liquid 19' overflows from the chamber area 10 to the overflow area 20, as denoted by arrows pointing outwards in FIG. 5. Note that numeral references are not necessarily repeated in FIGS. 2-6, for clarity. The drawings at issue are otherwise self-explaining.

Figure 3:
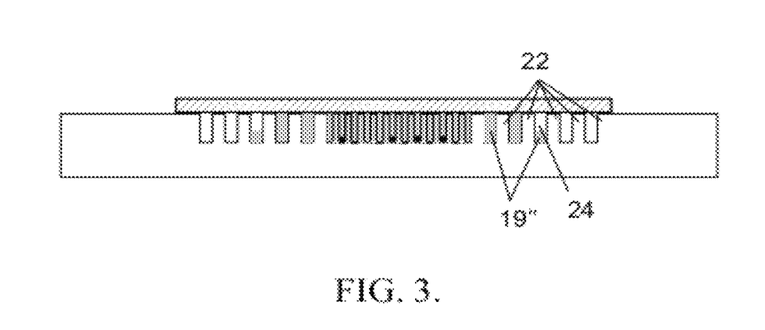
Figure 6:
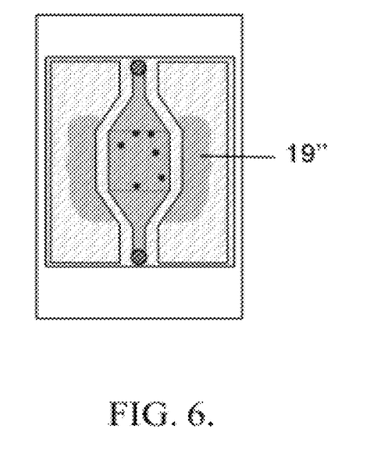

Once the cover has reached a closing position, as illustrated in FIG. 3 or 6, excess liquid 19" stabilizes in the overflow area, where it is retained in the space 24 left vacant by the capillary structures 22.

Accordingly, while the cells are mostly retained in the chamber, fluid can be removed from the chamber (or exchanged with another one) for other use, as to be discussed later. Most cells are likely to be retained in the chamber, thereby offering improved control of their consumption.

Basically, a volume of fluid suspension larger than that of the chamber can be deposited, the excess fluid being easily evacuated to the overflow area, without substantial loss of cells. Incidentally, it can be noted that the density of cells at the level of the chamber area increases when passing from FIGS. 1 to 3. Note that minimizing the loss of cells is sometimes critical.

Removing excess fluid from the chamber is advantageous in many respects. For example, the liquid 19" captured in the overflow area 20 may be used for maintaining the cover in a close position, by capillarity, as illustrated schematically in FIG. 3. To this aim, the capillary structures 22 are configured such that liquid 19" retained therein can itself retain the cover in the said close position.

Several device configurations may be contemplated in that respect. For instance, the device 100 may be configured such as to allow for a constant, thin layer of liquid to wet the overflow area 20. In particular, the capillary structures and at least some of the chamber features may be co-planar, as depicted in FIGS. 1-3. The capillary structures may further have dimensions conveniently chosen and be distributed according to optimal structure patterns, as described later in reference to FIG. 8.

Figure 7:
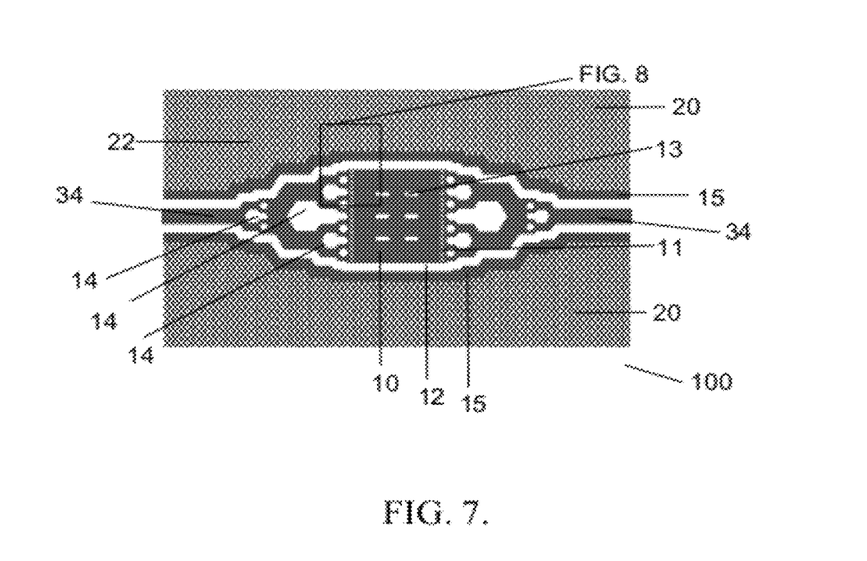
FIG. 7 is a top view of a portion of the device of FIGS. 1-6, showing more details thereof.

Next, FIG. 7 shows a schematic top view of an inner part of the device of FIGS. 1-6. Note that the device is rotated, in comparison with FIGS. 4-6. In addition, attention is drawn to those white features, which represent solid structures while grey/black zones denote empty space, at variance with previous drawings.

Yet, just as before, the drawing illustrates the chamber 10, open on the top (towards the reader's eyes), and delimitated notably by retention features 11 and lateral walls 12. Here, the walls 12 of the chamber are further shaped such as to define fluid passages 34 extending up to opposite ends of the chamber 10. The passages at stake may have different use, as shall be discussed later. The device further shows an overflow area 20, having capillary structures 22. In the embodiment of FIG. 7, the overflow area 20 is located substantially at the periphery of the chamber 10, merely surrounding it. Such a configuration allows for the capillary structures 22 to retain excess liquid overflowing from the chamber 10. The cover is not shown here.

In addition, with respect to the previous figures, more details are now apparent. In particular, the chamber 10 as depicted here further comprises distribution structures 14. The said structures are configured to distribute a liquid flow in the chamber. In this respect, a liquid flow may have to be maintained in the chamber for preserving or servicing the cells. As the chamber 10 is larger than the passages 34, it is beneficial to make sure that cells anywhere in the chamber be properly exposed to the incoming liquid. This is particularly important because at scales in the range of one millimeter and below, flow of liquid tends to be laminar. With laminar flow, turbulences and strong mixing are unlikely to occur. Thus, providing the chamber with flow distribution features helps preventing uncontrolled, non-uniform flow in the chamber. One or more of such distribution features may be provided, preferably configured with respect to a direction of incoming liquid flow, at locations where the volume accessible to the fluid increases, as illustrated in FIG. 7.

As can further be seen in FIG. 7, the retention features 11 in the chamber do not necessarily have to encircle the chamber. They may for instance partly delimitate the chamber, e.g. perpendicularly to the passages 34 mentioned earlier, to retain the cells from liquid flowing outwardly.

The chamber may further be preferably provided with support features 13, to support the cover in the said "close position" and prevent local deformations of the cover, especially when positioning it.

Interestingly, a dewetting zone 15 may further be provided, as depicted in FIG. 7. The dewetting zone is located between the chamber 10 and the overflow area 20; here its shape closely reflects that of the walls 12. The dewetting zone was not depicted in the previous figures, for clarity. It is not even critical. However, such a zone can be designed to provide a suitable transition medium for liquid overflowing from the chamber to the overflow area.

Figure 8:
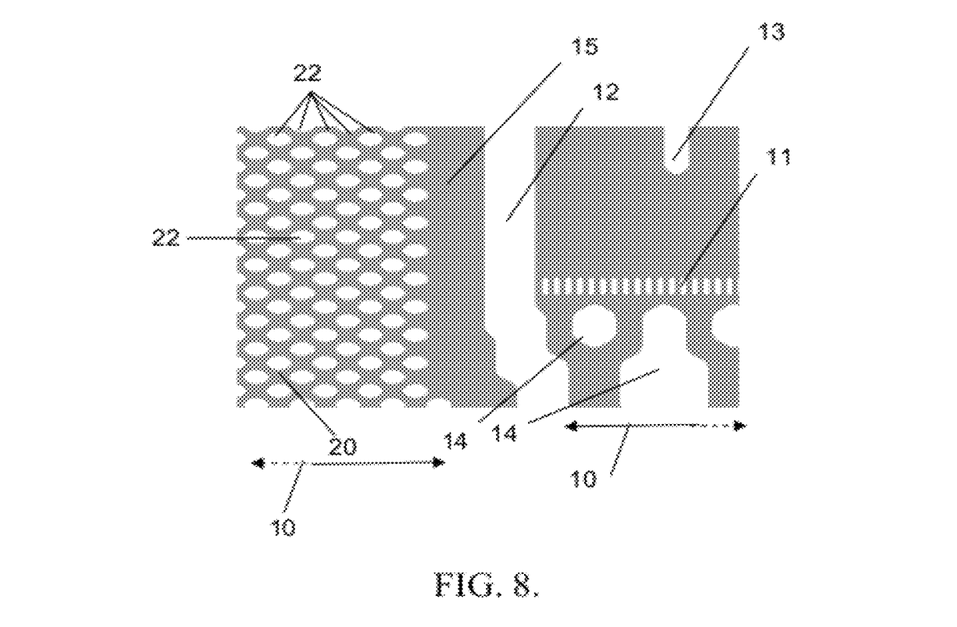
FIG. 8 focuses on a specific portion of FIG. 7, as indicated therein.

In the example of FIGS. 7-8, the dewetting zone is a zone around the main wall 12 of the cell chamber 10, deprived of any particular structures. It is merely flat. Its purpose is to separate the capillary structures 22 sufficiently from the main wall 12 in order to provide a zone of low capillary pressure. In particular, it may be configured such that a capillary pressure of a liquid therein is lower than the capillary pressure in the overflow area 20 (in absolute term).

This makes the liquid in the dewetting zone moving to the capillary structures. Ideally, all liquid in the dewetting zone would move to the capillary structures. Otherwise, if too much liquid remains in the dewetting zone, there is a risk for the liquid to move back to the chamber 10 via a residual space between the cover and the main wall 12. This is all the more possible if the cover is substantially hydrophilic (e.g. it has an advancing contact with water≤45°. For this reason, it was concluded that the minimal width of the dewetting zone should preferably be at least twice the smallest distance separating two adjacent capillary structures.

When the liquid begins overflowing from the chamber 10 (as depicted in FIG. 2 or 5), the dewetting zone is able to receive and store the excess liquid, without opposing much resistance thereto. Next, when the overflowing liquid begins penetrating the surrounding capillary medium 20, the differential of capillary pressures naturally prompts it to move from the dewetting zone towards the capillary medium 20.

How to achieve this shall be discussed next, in reference to FIG. 8, which highlights the rectangular portion shown in FIG. 7. Note that FIG. 8 is rotated back with respect to FIG. 7, such that the same orientation as in previous FIGS. 4-6 is restored.

Several features as described above are still to be seen, such as the chamber area 10, support features 13, cell retention features 11, distribution features 14, and the wall 12. Beyond the dewetting zone 15, the capillary structures 22 in the overflow area 20 are depicted in more details.

In particular, the capillary structures 22 as in the embodiment of FIG. 8 define a regular arrangement of structures 22 in space, comparable to a 2D crystallographic lattice. Specifically, the capillary structures 22 here define a lattice with 50% compactness. In other words, the lattice allows for filling 50% of its total surface with the liquid retained therein. This ratio appears optimal in practice, not only in terms of manufacture, but also for wetting and retaining e.g. water. Yet, substantially lower or larger ratio (such as 30% or 70%) may still be suitable, depending on the liquid chosen, the microorganisms studied, etc.

In addition, as illustrated, the average separation distance between capillary structures in the lattice is preferably less than 500 micrometers (μm), for enabling capillarity retention. Yet, choosing this distance less than 200 μm improves the performance of the capillary lattice. Even, a distance of about or less than 60 μm optimizes the manufacturability vs. performances of the device.

With such average separation distances (less than 500, 200, or 60 μm), and provided that a convenient choice of material is made (e.g. PDMS with surface treatment), the advancing contact angle accordingly provided by the capillary structures (e.g. with water) is less than 90°, less than 60°, or less than 45°, respectively.

In the case of PDMS, which has an advancing contact angle with water slightly above 90°, a simple surface treatment can be applied to the PDMS to make it hydrophilic. One treatment is to deposit cell adhesion molecules onto the PDMS surface. This can be done before loading a solution containing cells in the chamber 10. For example, a PDMS microorganism culture device 100 can be covered with an aqueous biological buffer containing fibronectin for 30 min. The culture device can then be rinsed with deionized water and dried using a stream of air. This will result in the spontaneous deposition of a layer of fibronectin molecules everywhere on the PDMS surface. As a result, PDMS will be hydrophilic due to the presence of the fibronectin on its surface. In addition, the treated PDMS surface will promote the adhesion and proper biological development of cells because fibronectin is a cell adhesion molecule. Other cell adhesion molecules can be used. Similarly, other treatments are possible such as for example depositing a surfactant or block copolymer on the PDMS surface.

The capillary structures may have suitable dimensions and shapes and be distributed according e.g. to a rhombic, hexagonal or a parallelogrammic lattice, which are known per se. For instance, the capillary structures shown in FIG. 8 match an hexagonal lattice. They further have oblong shapes with length of e.g. 100 μm and width of 60 μm. Here, the intra-row spacing is 60 μm, twice as much the inter-row spacing (30 μm). Remarkably, the first row is 215 μm away from the main wall 12, so the width of the dewetting zone 15 is 215 μm in this case.

Note that the dimensions above are indicative only. An optimal choice depends on the material and liquid involved, as shall be apparent to one skilled in the art. Yet, the material, dimensions and shape of features in the device may preferably be tuned in order to optimize the various capillary pressures involved.

Concerning their shapes, the capillary features preferably have one or more rounded walls, to prevent pinning of the liquid on corners. Furthermore, as evoked, they preferably have an oblong shape, with their main axis oriented as much as possible along the expected direction of overflow of the liquid. Here, the main axis of the oblong features is merely perpendicular to the main wall 12. This allows for optimizing the dragging of liquid away from the wall 12 and not mostly parallel to it. Also, the lateral size of and separation distance between the capillary structures are tuned to optimize the capillary pressure.

In addition, the capillary structures may preferably have substantially the same height as some or all of the features in the chamber (walls, retention features, support features, etc.), as apparent in FIG. 1. Having the same height simplifies the fabrication process because all structures are etched in the same step to the same depth. So the depth in the area 20 can be fixed to be the same as in the chamber 10.

Next, the cover is preferably transparent, for experimental reasons, as evoked in introduction. Owing to the capillary structures, e.g. as described above, the cover may further possibly be self sealable on the device. Even more preferably, the cover can be removable and re-positionable, which nicely improves ergonomics of the device. To this aim, it is advantageously provided e.g. as a flexible lid. In operation, the cover can accordingly be first moved to a close position. Next, it can be removed, for subsequent intervention in the device. Hence, a given property of the liquid in the device can easily be modified. The cover may for instance be removed for recovering some of the cells, e.g. by direct aspiration using a pipette. The recovered cells can then be analyzed, cultured or modified elsewhere than on the cell chamber. Or the cover can be removed if specific measurements had to be done on the cells, which e.g. requires inserting probes in the chamber. For example the cover may be removed and a pipette for patch clamp measurement or a microelectrode for impedance measurements can be brought in contact with one cell of interest. Finally, one may close the device again with the cover.

As discussed earlier, e.g. in reference to FIG. 7, the chamber may comprise one or more liquid passages 34, allowing at least closed circulation of the liquid through the chamber, inside the device. Now, the cover may further comprise one or more vias 32 connectable to the passages, e.g. when the cover closes the device. Accordingly, the vias may allow for filling some sample or additional fluid, or regulating the fluid already in the device even after closing the cover, be it for preserving living cells in the chamber. In practice, one typically monitors the cells before and after interaction with the added sample. One via 32, at one end, can hence be used for insertion of the sample, and the other via 32, at the other end, for evacuation thereof. The vias 32 are thus used for maintenance, regulation of microorganisms in the device. Other vias can further be provided, which shall be described later.

Having vias 32 as described above provides a number of advantages. In particular, this markedly simplifies the fabrication of the device as it dispenses with tunneling structures with rounded profile in the body of the device, which is likely difficult. In addition, this allows for easily adapting the diameter of the opening on the vias, if necessary. Yet, should a substantial intervention be needed in the chamber, like recovering some of the cells, it is still possible to remove the cover.

Moreover, external peripheral equipment such as pumps, heaters, and valves can be connected to the vias 32. This permits flowing liquids in the cell culture device 100 with different flow rates, for various durations. Liquids can even be flowed so as to form gradients in the cell chamber 10. The possibility to connect the cell culture device 100 to external equipment greatly enhances its use and functionality by allowing a broad range of simple and complex studies on cells to be performed. Not having connectivity to external equipment would otherwise require implementing the needed function to the cell culture device 100 thereby making the device much more costly and complex to fabricate and use.

Figure 9:
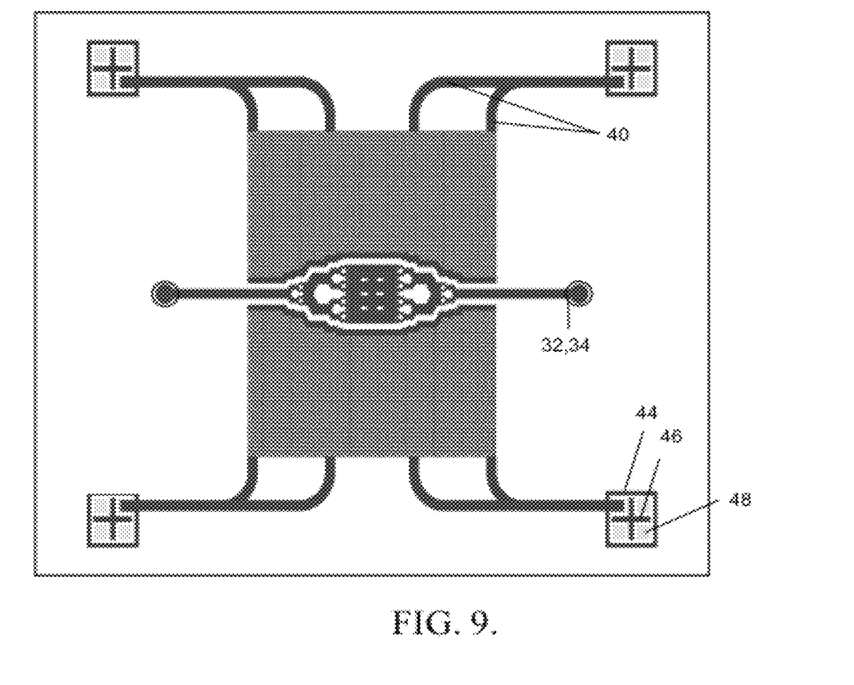
FIG. 9 illustrates a larger portion of the device as viewed in FIG. 7.

Next, FIG. 9 illustrates a larger portion of the same device as in FIG. 7, wherein more features can be seen. As before, the chamber and the overflow area are represented. Although not explicitly depicted, the cover is assumed to be set onto the device, such as to close it. Vias 32 are located upright the ends 34 of the passages, as discussed, and connected thereto. Suitable connections are known per se. Standard 1/32-inch tubes with fittings and adapters from Upchurch Scientific® may for instance be used.

In addition, vents 40 are preferably provided, which are configured to remove excess fluid (air or liquid) from the capillary structures. Basically, air bubbles are thereby prevented. In fact, closing the device with the cover may lead to local overpressure, resulting in turn in the formation of air bubbles under the cover. Air bubbles, which may impair subsequent observations, are thus advantageously prevented with vents.

To this aim, vents may be connected in several places to edges of the capillary area, as depicted in FIG. 8. Vents 40 lead to outlets 44. Advantageously, alignment marks 46 may be provided at the level of the outlet 44, in order to help adjusting the cover when closing the device. Additional vias 48 can be provided in the cover, which connect to the outlets 44. This allows for moving excess fluid, like air, from the overflow area, successively through the vents 40, outlets 44 and vias 48 to the outside.

Figure 10:
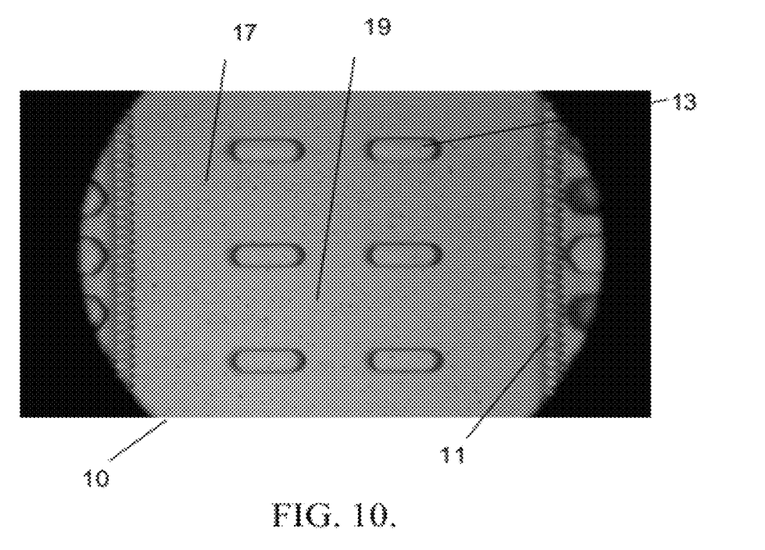
FIGS. 10-11 are snapshots obtained from a film of the operation of a culture device, according to an embodiment of the invention.
Figure 11:
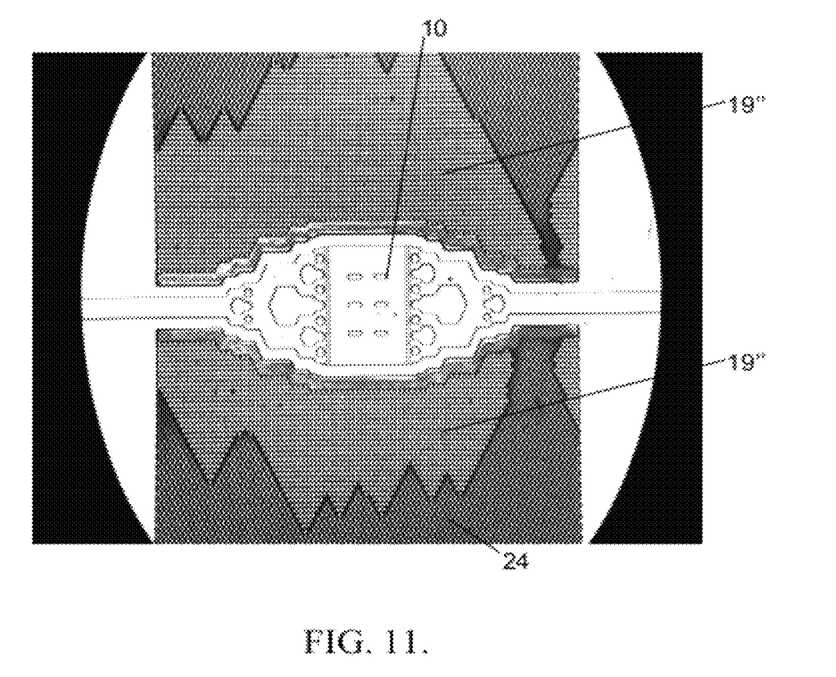

Next, FIGS. 10-11 are snapshots extracted from a film showing the device in operation. FIG. 10 focuses on the inner chamber 10, showing notably the cell retention features, and supports 13. Flow distribution features are partly visible, behind the cell retention features. A liquid suspension 19 has been deposited. It is mostly transparent and hence barely visible. Yet, cells 17 are already perceptible in the snapshot. In particular, the cells are living microglia, cultured in the chamber 10. The chamber as of FIG. 10 is already sealed with a cover, here a Si chip (the cover was microfabricated in a Si wafer). The cell culture device was molded in PDMS. Imaging was obtained with an optical microscope (images are viewed through PDMS using an inverted microscope).

FIG. 11 is a lower magnification snapshot, revealing most details of a device as discussed above. At the time of the snapshot, the cover is being sealed onto the device. In accordance with FIGS. 2 and 3, liquid is being pushed towards the overflow area 20. The snapshots allows to distinguish amongst zones of the overflow area wherein liquid 19" is retained and zones wherein capillary recesses 24 are not yet wetted by the liquid. Remarkably, the progression of the overflowing liquid is partly determined by the symmetry of the lattice. Accordingly, the lattice can be chosen in consideration of the overall basal shape of the device, or reciprocally, in order to optimize the progression of the overflowing liquid.

In the present case, one can realize that a large area can be wetted by the liquid 19", thereby ensuring a safe capillary seal with the cover.

In the embodiment pertaining to FIGS. 10-11, the device is a microfluidic culture device. The problem of studying cells is solved by culturing cells in an open microfluidic that can be sealed with a cover, by capillarity. The device as shown here also solves the problem of forming a well defined optical interface for studying living cells. In addition:

- cells can be easily seeded in the cell chamber and cultured similarly as in methods using culture dishes (renewal/exchange of medium is similarly simple, temperature and $CO_2$ controlled using e.g. cell incubator);
- for observation and/or experiments, a sealing cover is added;
- the cell chamber and the cover are preferably designed for sealing well (no air trapped, excess liquid/air is possibly moved from the sealing areas via vents);
- the cell chamber is adjacent to overflow capillary structures (yet separated via a dewetting zone);
- the cell chamber has retention features, which help retaining cells that are seeded in the chamber;
- the cell chamber has flow distributing structures and closed fluid passages;
- the sealing cover has vias connecting at ends of the passages and vents, e.g. to connect the system to e.g. pumps, once closed;
- The cell chamber and sealing cover are designed to efficiently assemble;
- No or little air is trapped. In this respect, the vias of the sealing cover and tubings connected to the sealing cover may advantageously be prefilled; and
- Excess liquid in the chamber is moved to the overflow structures during sealing.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

For example, it has merely been considered here that a liquid portion (i.e. a convex meniscus) would likely protrude from the chamber after deposition, and before being pressed while closing the device. In a variant, one may contemplate embodiments where the device and the deposited liquid are such that capillary pressures result in excess liquid overflowing from the chamber immediately after deposition, even before closing the device. Accordingly, other material than PDMS, Si and water could be involved.

The invention claimed is:

1. A microorganism culture device, comprising:
an open chamber having microorganism retention features, wherein the open chamber retains at least one microorganism;
an overflow area surrounding the open chamber, comprising capillary structures configured to retain, in operation, excess liquid overflowing from the open chamber, the capillary structures defining a lattice with a compactness ratio configured to retain the excess liquid in space between outer surfaces of the capillary structures; and
a dewetting zone deprived of any particular structures and having a width separating a wall of the chamber and the overflow area, wherein the width of the dewetting zone is greater than the space between the outer surfaces of the capillary structures such that a capillary pressure in the dewetting zone is lower than a capillary pressure in the overflow area, in absolute term.

2. The device of claim 1, wherein:
the overflow area is an open area, the chamber and the overflow area have a same open side;
the device further comprises a transparent cover movable to a close position where it covers the open side; and
the capillary structures are further configured such that liquid retained by the capillary structures retains the cover in the close position, by capillarity.

3. The device of claim 2, wherein the device is configured such that the cover is self sealable on the device.

4. The device of claim 2, wherein:
the chamber comprises one or more liquid passages allowing closed circulation of the liquid inside the device; and
the cover comprises one or more vias connectable to the passages in the close position.

5. The device of claim 1, wherein the capillary structures define a lattice allowing for filling at least 30% of a surface of the lattice with liquid retained in the lattice.

6. The device of claim 1, wherein the chamber further comprises one or more distribution structures configured to distribute a liquid flow in the chamber.

7. The device of claim 1, wherein the device is a microfluidic culture device.

8. The device of claim 1, wherein the device further comprises vents configured to remove, in operation, excess fluid from the capillary structures.

9. The device of claim 1, wherein the overflow area is substantially at a periphery of the chamber.

10. The device of claim 1, wherein the capillary structures define a lattice allowing for filling at least 50% of a surface of the lattice with liquid retained in the lattice.

11. The device of claim 3, wherein:
the chamber comprises one or more liquid passages allowing closed circulation of the liquid inside the device; and
the cover comprises one or more vias connectable to the passages in the close position.

12. The device of claim 1, wherein an average separation distance of the capillary structures is less than 60 μm.

13. The device of claim 1, wherein:
the overflow area is an open area, the chamber and the overflow area have a same open side; and
the wall limits flow of liquid between the open chamber and the overflow area to liquid passing through the open side.

14. The device of claim 1, wherein an average separation distance of the capillary structures is less than 200 μm.

* * * * *